US011931547B1

(12) United States Patent
Kriheli et al.

(10) Patent No.: US 11,931,547 B1
(45) Date of Patent: Mar. 19, 2024

(54) DEVICES FOR USE IN DRUG DELIVERY SYSTEMS

(71) Applicant: Equashield Medical Ltd, Migdal Tefen (IL)

(72) Inventors: Marino Kriheli, Savion (IL); Raanan Tavor, Yuvalim (IL); Eric Shem-Tov, Ramat Hasharon (IL); Shlomi Dach, Qiryat Yam (IL)

(73) Assignee: Equashield Medical Ltd (IL)

( * ) Notice: Subject to any disclaimer, the term of this patent is extended or adjusted under 35 U.S.C. 154(b) by 0 days.

(21) Appl. No.: 18/286,859

(22) PCT Filed: Apr. 14, 2022

(86) PCT No.: PCT/IL2022/050399
§ 371 (c)(1),
(2) Date: Oct. 13, 2023

(87) PCT Pub. No.: WO2022/219638
PCT Pub. Date: Oct. 20, 2022

(30) Foreign Application Priority Data

Apr. 14, 2021 (IL) .......................................... 282356

(51) Int. Cl.
*A61M 5/162* (2006.01)
*A61M 39/10* (2006.01)

(52) U.S. Cl.
CPC ........ *A61M 5/162* (2013.01); *A61M 39/1011* (2013.01)

(58) Field of Classification Search
CPC ............ A61M 5/162; A61M 2205/332; A61M 2039/0081; A61M 39/1011; A61M 39/10; A61M 39/20; A61M 39/06; A61J 1/2089; A61J 1/2006; A61J 1/20; A61J 1/1481; A61J 1/1487; A61J 1/2048
See application file for complete search history.

(56) References Cited

U.S. PATENT DOCUMENTS

| | | |
|---|---|---|
| 2,834,346 A | 5/1958 | Adams |
| 3,685,680 A | 8/1972 | Shilipetar et al. |
| 4,515,752 A | 5/1985 | Miramanda et al. |
| 5,312,363 A | 5/1994 | Ryan et al. |
| 6,551,283 B1 | 4/2003 | Guo et al. |

(Continued)

FOREIGN PATENT DOCUMENTS

| | | |
|---|---|---|
| EP | 0573102 A1 | 12/1993 |
| EP | 1492590 B1 | 7/2007 |

(Continued)

OTHER PUBLICATIONS

International Search Report for PCT/IL2022/050399 dated Jul. 31, 2022.

(Continued)

*Primary Examiner* — Theodore J Stigell
(74) *Attorney, Agent, or Firm* — Whitestone Law, PLLC

(57) ABSTRACT

Some embodiments are directed to a medical device for fluidly connecting to a medical spike, including a spike port configured to receive therein the medical spike and establish fluid communication between the medical spike and the medical device The spike-locking mechanism can be configured to resist extraction of the medical spike from the spike port.

20 Claims, 8 Drawing Sheets

(56) References Cited

U.S. PATENT DOCUMENTS

| | | |
|---|---|---|
| 7,744,581 B2 | 6/2010 | Wallen et al. |
| 9,039,672 B2 | 5/2015 | Wallen |
| 2003/0191445 A1 | 10/2003 | Wallen et al. |
| 2004/0211484 A1 | 10/2004 | Fournie et al. |
| 2005/0182383 A1 | 8/2005 | Wallen |
| 2010/0168712 A1 | 7/2010 | Tuckwell et al. |
| 2018/0028402 A1 | 2/2018 | Kriheli et al. |

FOREIGN PATENT DOCUMENTS

| | | | |
|---|---|---|---|
| KR | 2011010658 | * | 9/2011 |
| KR | 20110106158 A | | 9/2011 |

OTHER PUBLICATIONS

Written Opinion of the International Searching Authority for PCT/IL2022/050399 dated Jul. 31, 2022.
International Preliminary Report on Patentability for PCT/IL2022/050399 dated Aug. 8, 2023.

* cited by examiner

DEVICES FOR USE IN DRUG DELIVERY SYSTEMS

CROSS REFERENCE TO RELATED APPLICATIONS

This application is a national phase filing under 35 C.F.R. § 371 of and claims priority to PCT Patent Application No. PCT/IL2022/050399, filed on Apr. 14, 2022, which claims the priority benefit under 35 U.S.C. § 119 of Israeli Patent Application No. 282356, filed on Apr. 14, 2021, the contents of each of which are hereby incorporated in their entireties by reference.

TECHNOLOGICAL FIELD

The presently disclosed subject matter is in the medical field and relates to devices for use in drug delivery or transfer systems; particularly, the presently disclosed subject matter relates to adaptors and devices for connecting between different parts of the drug delivery system to enable the drug transfer therethrough.

BACKGROUND

Drug delivery systems, such as infusion systems, should transfer the drug, specifically a hazardous drug, in a safe manner while preventing, or at least minimizing, exposure of the drug to the environment and the people involved whether the staff or the patient.

Accordingly, the various devices used with or in the drug delivery system, such as adaptors and drug transfer devices, should provide complete sealing and eliminate any possibility for leak of the drug being transferred along the way.

Additionally, the devices should provide a tight, preferably hermitic, connection to the other parts of the system and prevent accidental, or sometimes intentional, disconnection therebetween during use.

Drug delivery systems are typically configured for a single use only, thus making them from disposable, light and drug-compatible, materials while ensuring their rigidity and contamination-free qualities is desired.

GENERAL DESCRIPTION

The presently disclosed subject matter provides devices for use in drug delivery or drug transfer systems. The disclosed devices are configured for easy handling, are extremely safe for the user (staff and patient) in that they at least provide a reliable, tight, connection throughout the system and a fully effective sealing during use.

Typically, a medical spike is inserted into and extracted from a spike port under friction forces applied by the spike port, specifically the spike port's internal walls, on the spike. The insertion as well as the extraction movements are referred to as twist-off movements in which the spike is rotated and twisted during the insertion and extraction actions. It is noted that, typically, once the medical spike is inserted and safely located inside the spike port, it is intended to be kept thereinside and to be dismissed altogether after a single use. The friction forces applied on the medical spike, by the spike port, are aimed at keeping the medical spike connected and securely located inside the spike port and to prevent the spike from exiting therefrom.

The above technique involves several disadvantages. Firstly, certain, non-small, amount of insertion force must be applied on the spike by the medical staff, in order to overcome the friction forces during the insertion action. It is appreciated that the greater the friction the better the holding of the spike inside the spike port. Therefore, the applied insertion force can sometimes cause pain and, at less frequent cases, damage to the hands of the medical staff. The chance of developing pain and causing damage increases with the repetitive insertion actions performed on usual basis. Secondly, application of the insertion force on the spike may sometimes cause damage to the spike itself. In this case, extraction of the damaged spike, which is also subject to non-small extraction force applied by the medical staff, and another insertion action of a new spike with the above-mentioned risks, are required. Thirdly, at times, the spike is not held securely inside the spike port and accidental extraction of the spike out of the spike port, whether intentionally or unintentionally, may occur being accompanied with undesired exposure of the drug to the environment.

The presently disclosed subject matter provides a technique that enables securely locking the spike inside the spike port and eliminates the risk of accidental extraction of the spike from the spike port even under application of a relatively big extraction force.

Specifically, the presently disclosed subject matter provides medical devices, and more particularly, spike ports configured to receive therein medical spike for fluidly connecting the medical device to the medical spike. In conventional ports the friction between an inner surface of the spike port and an outer surface of the spike functions as spike holding mechanism that resists the spike from being accidentally falling off the medical device. However, such friction also contributes in making the insertion, and thus connection, of the spike into the spike port. The spike port as described herein eliminates to a great extent the friction between the port and the spike thereby resulting in a much easier (with much lesser insertion force) insertion of the spike in the spike port. The friction between the portions of the spike port contacting the spike and the spike can further be reduced by using low friction material like Teflon added on top of an interior surface of the spike port and/or lubricants such as silicone oil on the medical spike itself. Simultaneously, the spike port is configured to resist, even with the reduced friction, the extraction of the spike from the spike port since the force required for extracting the spike from the port is at least thrice the force required for insertion of the spike for connecting to the spike port. In one example, the spike port comprises a spike-locking mechanism to lock the spike inside the spike port thereby provide above-mentioned resistance to the extraction of the spike from the spike port. The spike-locking mechanism also provides stabilization to the medical spike when received inside the spike port.

Further, the spike port can have a spike sealing element, while the spike includes or not the spike-locking mechanism, configured to seal the interior of the spike port from the exterior thereof when the spike is received within the spike port. The spike sealing element though is configured primarily for sealing the fluid flow and is not specifically configured to contribute to either stabilization or locking of the medical spike inside the spike port. For instance, the spike sealing element can be configured to offer a very low friction to the spike when inserted/extracted into/out of the spike port. In one implementation, especially when the spike port does not include the spike-locking mechanism, the spike port can have a port inlet having a narrower cross-section as compared to its adjacent regions configured to support and stabilize the spike when received inside the port.

Therefore, it is to be understood herein that according to the presently disclosed subject matter, the spike port offers an easy insertion to the spike, while providing the required sealing, and difficult extraction thereto without involving the friction between the port and the spike. Also, the spike port can stabilize the spike inside the port by the locking mechanism and/or a narrowed port inlet. The spike port can also have a spike sealing element sealing the fluid flow out of the spike port, said spike sealing element not necessarily contributing to the locking and or stabilization of the spike. Thus, it is to be understood that the spike port described according to various aspects and examples below can have the features concerning one or more of easy insertion of the spike, difficult extraction of the spike, sealing the fluid flow out of the port, and stabilizing the spike in various combinations of the aspects and examples detailed in this application.

In accordance with a first aspect, the presently disclosed subject matter discloses a medical device for fluidly connecting to a medical spike, the device comprising: a spike port configured to receive therein the medical spike and establish fluid communication between the medical spike and the medical device; and a spike-locking mechanism configured to resist extraction of the medical spike from the spike port.

A medical spike, or simply spike, as used herein in this application, refers to a generically known spike used in medical applications at the end of one part of a drug delivery/transfer system to enable serial connection of that part to another part of the drug delivery/transfer system. Specifically, medical spikes are built in accordance with known and acknowledged standards, such as ISO 18250-7:2018 and ISO 8536-4:2019, and is occasionally referred to as closure-piercing device. The spike's physical properties, such as the dimensions, tensile strength, insertion and extraction forces into and out of a corresponding spike port, are defined and known.

The sealing element of the presently disclosed subject matter can be configured to seal the interior of the spike port from the exterior of the spike port in such a manner that when a test spike, in accordance with ISO 8536-4, remain inserted in the spike port for 5 hours, and then an interior of the spike port distal to the sealing element is subjected to gauge pressure of 20 kPa for 15 seconds, no leakage occurs.

It is noted that extraction force/action of spike from the spike port, as referred to herein, includes both intentional (e.g. by pulling), unintentional extraction force/action, such as falling if the device, and natural forces such as gravitation. Further, the extraction forces can be axial and/or rotational (twist off) forces. Also noted, the spike port has a port longitudinal axis along which the spike is inserted. Since the spike also has a spike longitudinal axis, the spike is inserted into the port such that both the port and spike longitudinal axes coincide.

The spike port according to the first aspect can include on or more features of the below mentioned features concerning the operation of the locking mechanism:
- the spike-locking mechanism can be located inside the spike port;
- said spike-locking mechanism can be configured to be activated, to thereby lock the medical spike inside the spike port for resisting the extraction thereof, in response to initiation of extraction of the medical spike out of the spike port;
- said spike-locking mechanism can be configured to be activated automatically in response to initiation of extraction of the medical spike out of the spike port;
- said spike-locking mechanism can be switchable from an unlocking state in which insertion of the medical spike into the spike port is allowed, and a locking state in which extraction of the medical spike from the spike port is resisted;
- said spike-locking mechanism can be switchable from said unlocking state to said locking state in response to initiation of the extraction of the medical spike out of the spike port; and
- said spike port can comprise a proximal port inlet, a distal port end and a port longitudinal axis extending between said port inlet and distal port end, said spike-locking mechanism comprising a spike-locking element positioned between said proximal port inlet and said distal port end.

According to a second aspect of the presently disclosed subject matter, there is provided a spike-locking mechanism configured to be received within a spike port of a medical device and resist extraction of a medical spike when received within the spike port, the spike-locking mechanism being switchable from an unlocking state in which insertion of the medical spike into the spike port is allowed, and a locking state in which extraction of the medical spike from the spike port is resisted, the locking state is automatically activated upon initiating extraction of the medical spike out of the spike port, to thereby lock the medical spike inside the spike port.

The spike-locking mechanism can comprise a spike-locking element configured to be positioned within the spike port between a proximal port inlet and a distal port end of the spike port.

The spike-locking element according to the first and/or the second aspect can include one or more of the features listed below:
- said spike-locking element can comprises an outer rigid portion and a movable portion extending inwardly from the rigid portion towards the port longitudinal axis and away from the proximal port inlet when positioned within the spike port, and configured to contact the spike and move further towards the port longitudinal axis as well as the proximal port inlet upon initiation of extraction of the medical spike out of the spike port, thereby resisting the extraction of the spike from the spike port;
- said movable portion can move along at least a radial direction towards said port longitudinal axis of the spike port;
- said movable portion of the spike-locking element can comprise at least one first inwardly projecting element inclined with respectively at least one first element angle defined with respect to a proximal portion of the port longitudinal axis and having respectively at least one first element distal portion that contacts the outer surface of the medical spike when located in the spike port, the first projecting element being configured to be activated by increasing the at least one first element angle upon application of an extraction force causing initiation of extraction of the medical spike out of the spike port such that the first element distal portion tightens its contact with the outer surface of the medical spike and resists the extraction of the medical spike from the spike port;
- said at least one first projecting element can comprise a plurality of first projecting teeth having a corresponding plurality of first tooth angles defining said at least one first element angle and a corresponding plurality of first tooth distal portions defining said at least one first element distal portion;

said movable portion of the spike-locking element can comprise at least one second projecting element having respectively at least one second element angle, defined with respect to the proximal portion of the port longitudinal axis, being greater than said at least one first element angle, and having respectively at least one second element distal edge, the at least one second projecting element being operatively connected to said at least one first projecting element in a way such that upon initiation of the extraction of the medical spike out of the spike port, the at least one first element moves towards the port longitudinal axis as well as the port inlet causing the at least one second projecting element to move at least towards the port longitudinal axis and the at least one second element angle to increase, thereby causing the at least one second element distal edge to contact the outer surface of the medical spike, thereby further resisting the extraction of the spike from the spike port;

upon further application of the extraction force, the at least second element distal edge can be configured to incise into outer surface of the medical spike, thereby further tightly resisting the extraction of the spike from the spike port;

said at least one second projecting element can comprise a plurality of projecting legs having a corresponding plurality of leg angles defining said at least one second element angle and a corresponding plurality of leg distal edges defining said at least one second element distal edge;

said spike-locking element can be configured to be positioned in a seating portion of and within the spike port and configured to freely rotate therein about the port longitudinal axis; and said tight contact between the at least one first element distal portion with the outer surface of the medical spike can cause the locking element to rotate when the spike is rotated.

The medical device according to the first aspect can further comprising a port cover member configured to selectively cover and uncover said port inlet.

According to a third aspect of the presently disclosed subject matter, there is provided a medical device configured for fluidly connecting to a medical spike, the medical device comprising: a spike port configured to receive therein the medical spike, said medical device being configured for fluidly connecting to said medical spike upon insertion thereof within the spike port with a first minimal force, said spike port being configured to resist the extraction of the medical spike from the spike port by a minimal second force at least three times greater than the first force.

Optionally, the second minimal force can define a minimum force required for extracting said medical spike from the spike port when the medical spike is connected to the medical device.

Optionally, the second minimal force can be at least four times greater than the first minimal force.

Optionally, the second minimal force is at least five time greater than the first force. Optionally, the first minimal force is at most 40N at an insertion rate of 500 mm·min$^{-1}$, when tested with a test spike in accordance with ISO 8536-4.

According to some examples, the first minimal force can be at most 35N at an insertion rate of 500 mm·min$^{-1}$, when tested with a test spike in accordance with ISO 8536-4, or can be at most 30N at an insertion rate of 500 mm·min$^{-1}$, when tested with a test spike in accordance with ISO 8536-4, or can be at most 25N at an insertion rate of 500 mm·min$^{-1}$, when tested with a test spike in accordance with ISO 8536-4.

Optionally, the second minimal force is at least 120N when measured with the same test spike as used for measurement of the first minimal force at a removal speed of 100 mm·min$^{-1}$.

In accordance with other example, the second minimal force can be at least 105N (when the first minimal force is 35N) when measured with the same test spike as used for measurement of the first minimal force and at a removal speed of 100 mm·min$^{-1}$, or can be at least 90N (when the first minimal force is 30N) when measured with the same test spike as used for measurement of the first minimal force and at a removal speed of 100 mm·min$^{-1}$, or can be at least 75N (when the first minimal force is 25N) when measured with the same test spike as used for measurement of the first minimal force and at a removal speed of 100 mm·min$^{-1}$, or can be at least 140N, 150N, or 175N (when the first minimal force is at most 40N) when measured with the same test spike as used for measurement of the first minimal force and at a removal speed of 100 mm·min$^{-1}$.

According to a fourth aspect of the presently disclosed subject matter, there is provided a medical device for fluidly connecting to a medical spike, the device comprising a spike port configured to receive therein said medical spike and establish fluid communication between the medical spike and the device; said spike port comprising: a port distal portion provided in a closed state and configured to be opened by a spike distal end of the medical spike during first insertion of the medical spike into the spike port; a port proximal portion configured to stabilize the medical spike when received inside the spike port; and at least one spike sealing element located between said port distal portion and said port proximal portion.

According to a fifth aspect of the presently disclosed subject matter, there is provided a medical device for fluidly connecting to a medical spike, the device comprising a spike port configured to receive therein said medical spike and establish fluid communication between the medical spike and the device; said spike port comprising: a port distal portion provided in a closed state and configured to be opened by a spike distal end of the medical spike during first insertion of the medical spike into the spike port; a port proximal portion; a port longitudinal axis extending between the port distal portion and the port proximal portion; and at least one spike sealing element located between said port distal portion and said port proximal portion, said port proximal portion comprising a seating portion configured to accommodate at least one spike-locking mechanism.

The spike sealing element can define a sealing minimal diameter of a cross-section taken perpendicular to the port longitudinal axis, said proximal inner surface portion defines a proximal maximal diameter of a cross-section taken perpendicular to the port longitudinal axis, said proximal maximal diameter being greater than the sealing minimal diameter; and The distal inner surface portion can define a distal maximal diameter of a cross-section taken perpendicular to the port longitudinal axis, said distal maximal diameter being greater than the sealing minimal diameter.

According to a sixth aspect of the presently disclosed subject matter, there is provided a medical device for fluidly connecting to a medical spike, the device comprising a spike port configured to receive therein said medical spike and establish fluid communication between the medical spike and the device; said spike port comprising: a port distal portion provided in a closed state and configured to be opened by a spike distal end of the medical spike during first insertion of the medical spike into the spike port; a port proximal portion comprising a port inlet, said port inlet defining an inlet minimal diameter of a cross-section taken perpendicular to the port longitudinal axis; and at least one spike sealing element located between said port distal portion and said port proximal portion, defining a sealing minimal diameter of a cross-section taken perpendicular to the port longitudinal axis, said port proximal portion defining a proximal maximal diameter of a cross-section taken perpendicular to the port longitudinal axis, said proximal maximal diameter being greater than both the inlet and the sealing minimal diameters.

The sealing minimal diameter can be greater than the inlet minimal diameter.

The port distal portion can define a distal maximal diameter of a cross-section taken perpendicular to the port longitudinal axis, said distal maximal diameter being greater than the sealing minimal diameter.

The port inlet can be more rigid than the spike sealing element.

The medical device according to the fourth, fifth, and/or sixth can include on or more of the features listed below:
- at least when said medical spike is fully inserted into said spike port, said at least one spike sealing element fully surrounds and engages an outer surface of said medical spike, thereby sealing the spike port and preventing fluid leakage from the spike port via the port proximal portion to an exterior of the device;
- said spike port can have a port inner surface facing an interior of the spike port, said port inner surface comprising a proximal inner surface portion corresponding the port proximal portion, and a distal inner surface portion corresponding the distal port portion;
- said at least one spike sealing element can be formed as a protrusion extending from the port inner surface towards a port longitudinal axis extending between the port distal portion and the port proximal portion;
- at least one of at least a majority of the proximal inner surface portion and at least a majority of the distal inner surface portion can be configured to be free of contact with the medical spike when received within the spike port;
- said at least one spike sealing element can form an integral part of the port inner surface;
- at least said port distal portion, said at least one spike sealing element and said port inner surface can be formed as a unibody member;
- said at least one spike sealing element can be made from a resilient material;
- said unibody member can be made from a resilient material;
- said resilient material can be a thermoset;
- said port distal portion can comprises a closed region;
- said closed region can comprise a weakened region configured to be punctured by the spike distal end during the insertion of the medical spike into the spike port, thereby opening the port distal portion; and
- said weakened region can have a thickness being less than a nominal thickness of the port distal portion.

The medical devices according to any of the fourth, fifth, and/or sixth aspects can include the locking mechanism according to any of the first and the second aspect having one or more features concerning the locking mechanism described for those aspects.

Further, according to any of the fourth, fifth, and sixth aspect, the locking element can be more rigid than the spike sealing element.

The medical device according to any of the first, third, fourth, fifth, and sixth aspect can further comprise a fluid inlet port and a first fluid duct connecting between said fluid inlet port and said spike port to thereby enable fluid communication between a fluid-containing device connected to said fluid inlet port and said medical spike located inside the spike port. Optionally, said fluid inlet port can be formed as a second medical spike being configured to be inserted into a matching port of the fluid-containing device and enable said fluid communication. Optionally, the medical device can further comprise: an injection inlet port configured to receive therein a fluid transfer device; and a second fluid duct connecting between said injection inlet port and said fluid inlet port to thereby enable fluid communication between said fluid transfer device and said fluid-containing device.

According to a seventh aspect of the presently disclosed subject matter, there is provided a medical device for transferring a drug therethrough, the device comprising: a housing comprising at least two housing portions connected to each other by a snap-fit connection, at least a first housing portion of the at least two housing portions being made from at least one first thermoplastic material; and at least one element being at least partially arranged inside the housing and configured for passing the drug through the device and being held by said snap-fit connection of the at least two housing portions, the at least one element being made from at least one second thermoplastic material that is drug-compatible and that has at least one of the following properties: has a lower stiffness than the at least one first thermoplastic material and is chemically inert.

Optionally, the at least one second thermoplastic material can have a lower physical property than said at least one first thermoplastic material, the physical property being at least one of the following: tensile strength, bending strength and hardness.

Optionally, the at least first housing portion can comprise protruding arms of said snap-fit connection, said protruding arms grasp corresponding snap-in portions formed in another housing portion of said at least two housing portions.

Optionally, the at least two housing portions can be made from the at least one first thermoplastic material.

Optionally, the at least one first thermoplastic material can be a drug-incompatible material.

Optionally, the at least one first thermoplastic material can comprise Acetal.

Optionally, the at least one second thermoplastic material can comprise one or more of the following: PVC-free material, polypropylene.

Optionally, the first housing portion can define an injection inlet port configured to connect to a fluid transfer device to receive the drug therefrom.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2C is a perspective view, FIG. 2D is a side view, FIG. 2E is a front view and FIG. 2F is a back view;

FIG. 4A is a perspective view illustrating a spike approaching the medical device of FIG. 1A, FIG. 4B is a perspective view illustrating the spike located inside the spike port of the medical device, FIG. 4C is an enlarged cross-sectional view illustrating the interaction between the spike and the sealing element of the spike port, FIG. 4D is a perspective view illustrating the spike locking state of the spike-locking element; FIG. 5A illustrates a snap-fit connection between two housing portions in a closed state, FIG. 5B illustrates the two housing portions separated; and FIG. 5C is an exploded view of the device of FIG. 4A.

DETAILED DESCRIPTION OF EMBODIMENTS

Figure 1A:
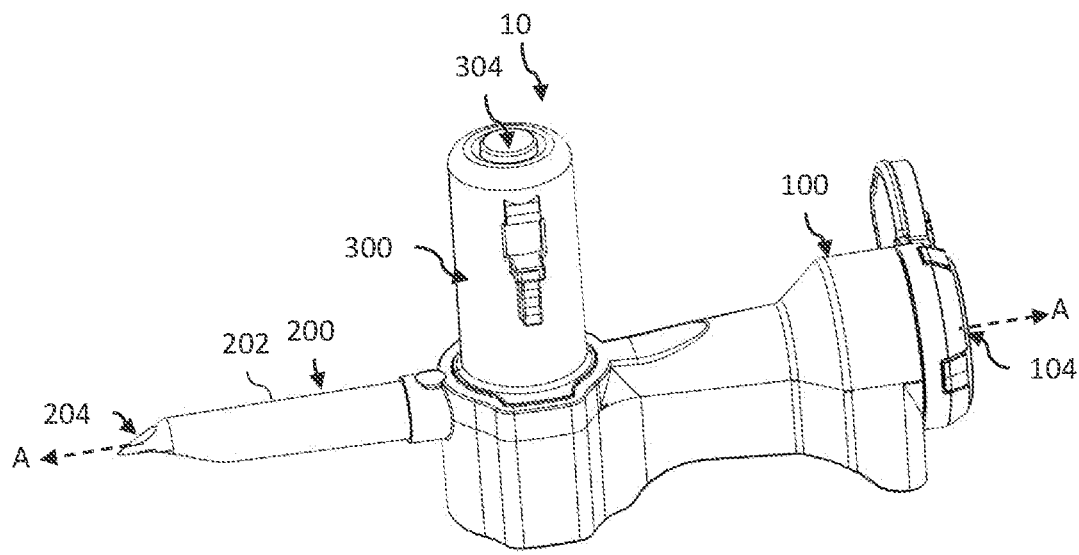
FIG. 1A is a perspective view of a non-limiting example of a medical device incorporating the presently disclosed subject matter.
Figure 1B:
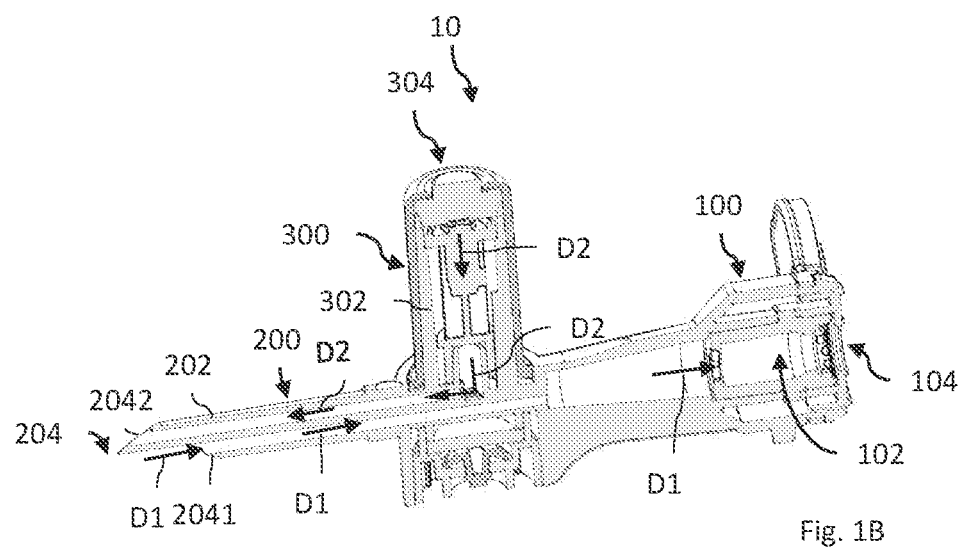
FIG. 1B is a cross-sectional view along line A-A of the medical device of FIG. 1A.

Reference is made to FIGS. 1A-1B showing a medical device 10 in accordance with a non-limiting embodiment of the presently disclosed subject matter. FIG. 1A is a perspective view of the medical device 10 and FIG. 1B is a cross section of the medical device 10 along the line A-A as illustrated in FIG. 1A. The medical device 10, in this non-limiting example, is a spike adaptor configured to be connected between at least two other devices, at a time, in order to establish a fluid connection therebetween when the medical device 10 is the intermediate device. It is noted that spike adaptors and their basic functionality are generally known in the art and are described herein briefly for the sake of clarity and completeness. The medical device 10 exemplified herein incorporates the aspects of the presently disclosed subject matter, as will be described herein below in detail. However, it is noted that describing the different aspects, especially with regard to the spike port, with reference to the medical device 10, being a spike adaptor in this specific example, should not limit the broad aspects of the presently disclosed subject matter that can be utilized and practiced in a variety of other medical devices that are not specifically mentioned herein, an example of which can be an IV bag, an adaptor, etc.

It is to be understood herein that all the examples of the medical devices exemplified herein, via their spike ports are configured to be used for connection with any standard spike irrespective of the shape and/or size thereof, whereas any such standard spike is built in accordance with known and acknowledged standards, such as ISO 18250-7:2018 and/or ISO 8536-4:2019.

As shown in the figures, the medical device 10 includes a body having three body portions 100, 200 and 300 each being terminated with at least one fluid inlet and/or outlet. The body portion 100 includes a spike port 102 configured to receive therein a medical spike, as illustrated further below, through a port inlet 104 and establish fluid communication between the medical spike and the medical device 10. The body portion 100 is therefore referred to as the spike receiving portion. The medical spike will basically form the inlet and/or outlet into a second medical device such as an infusion set configured to be connected to a patient body to transfer a drug thereto.

In some embodiments, the port inlet may not only serve as an opening through which the spike is introduced into the spike port but also as a spike stabilizer. In such cases, the port inlet includes an inlet edge extending symmetrically around the port longitudinal axis and which contacts a proximal portion of the outer surface of the spike when received inside the spike port, thereby stabilizing the spike and centralizing the spike along the port longitudinal axis inside the spike port. The inlet edge contacts the proximal portion of the outer surface of the spike when the spike is fully inserted into the port. It is to be understood herein that for the purpose of this description, the spike being fully inserted is intended to mean that the spike is inserted into the port to an extent necessary as well as enough for an effective connection of the spike with the port to establish the desired fluid communication between the medical device and the medical spike.

In other embodiments, the port inlet may not stabilize, or in fact may not even contact the medical spike when the spike is connected to the medical device. In such cases, the stabilization is provided by other means/elements as detailed further below.

The body portion 200 is configured as a second medical spike 202 terminated with at least one fluid inlet/outlet 204. Therefore, the body portion 200 is referred to as a spike terminal portion. The medical spike 202 is configured to be connected to a spike port of a third medical device and establish a fluid communication therewith via the at least one fluid inlet/outlet 204 such that a fluid communication is established between the third medical device and the medical device 10. For example, the third medical device can be a drug bag having a spike port (which can be configured in accordance with presently disclosed subject matter) that receives the spike 202 and such that a fluid communication is established, through the medical device 10, between the drug bag connected to the spike 202 and the patient connected to the spike received in the spike port 102. This exemplified fluid connection is illustrated by arrows D1 in FIG. 1B, the fluid route starts at the fluid inlet 2041, forming at least one fluid inlet/outlet at the end of the spike 202, and proceeds internally in the medical device 10 through dedicated ducts/channels until entering the medical spike received within the spike port 102.

The body portion 300 is configured as a fluid transfer device 302 utilizing a contamination-free fluid transfer, such as the techniques and devices described in WO08129550 assigned to the assignee of this application. The contamination-free fluid transfer device 302, referred to as a drug injection portion of the device 10, is terminated with a fluid inlet 304 configured to connect to an external second fluid transfer device, such as a syringe, to receive therefrom a fluid and transport it through the medical device 10, via dedicated internal ducts/channels, to another external device, such as a drug bag, connected to the spike 202 via fluid outlet 2042. The fluid inlet 304 can be configured as an injection fluid inlet configured to receive the fluid by injection from an injection device such as a syringe. The fluid path between inlet 304 and outlet 2042 is exemplified by arrows D2. This fluid transfer, controlled by fluid transfer device 302, can be used to transfer a drug into a bag drug, possibly containing another drug and where the different drugs mix, before connecting an infusion set to the spike port 102 to administer the mixed drugs to the patient.

Figure 2A:
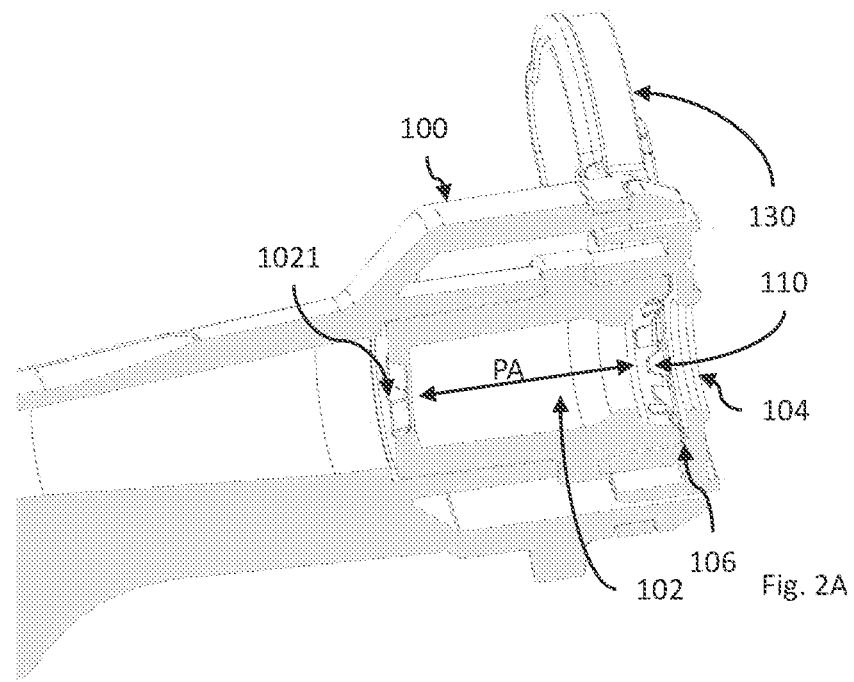
FIG. 2A is an enlarged view of the cross-sectional view of FIG. 1B, illustrating a non-limiting example of a spike-locking element according to a first aspect of the presently disclosed subject matter.
Figure 2B:
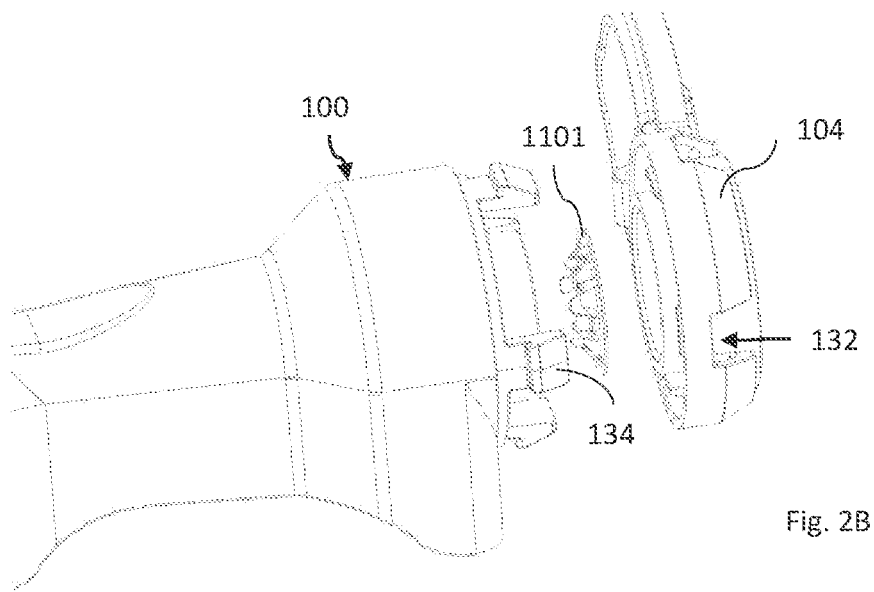
FIG. 2B is an exploded and enlarged view of a spike receiving portion of the medical device of FIG. 1A, illustrating the spike-locking element.

Reference is now made to FIGS. 2A and 2B illustrating a first aspect of the presently disclosed subject matter. FIG. 2A is an enlarged view of the cross section of the body portion 100 as shown in FIG. 1B, and the spike port 102. FIG. 2B is an exploded perspective view of some of the elements of the body portion 100. As shown, the spike port 102 includes at a proximal side thereof (i.e. the side closer to the port inlet 104), a spike-locking mechanism 110 that enables securely locking the spike, that is inserted into the spike port 102 along the port's longitudinal axis PA, inside the spike port 102, and consequently eliminates the risk of accidental extraction of the spike from the spike port 102 even under application of a relatively large extraction force. Accordingly, the spike port 102 provides resistance to extraction of the spike from the spike port 102.

In general, according to an example, the spike port is configured to allow an easy insertion of the medical spike into the spike port to fluidly connect the medical spike to the medical device. The spike port offers a resistance to insertion, by virtue a friction between in inner surface of the spike port and an outer surface of the spike and/or by the pierceable closed region within the spike port, of the spike therewithin that can be overcome by a first minimal force. In other words, the spike can be connected to the medical device when inserted into the spike port with a first minimal force. For the understanding of this description, the term connected with respect to fluid connection between the spike and the medical device is intended to mean that the spike is effectively connected to the medical device so as to be ready for use for transfer of drug. Thus, the first minimal force defines a minimum force required for insertion of the spike into the spike port for being connected to the medical device.

It is to be understood herein that the first minimal force, or in other words the force required for insertion of the spike into the spike port for connection, is measured at an insertion rate of 500 mm·min$^{-1}$, when tested with a standard plastic test spike, for example, one manufactured in accordance with ISO 8536-4.

The first minimal force described above is much less than the minimum force required for insertion of a medical spike (similar to ones referred to herein) in a conventional, known in the art, spike ports. The spike port according to the present description offers a much lesser friction to the spike during insertion than offered by the conventional spike ports. For instance, the spike port 102 (as described later herein below according to a non-limiting example) is configured such that a major portion of the inner surface of the spike port remains free of contact (does not contact) the spike when the spike is inserted into the spike port.

On the other hand, and simultaneously, the spike port is configured not to allow an easy extraction of the spike from the spike port. In other words, the spike port is configured to make the extraction of the spike from therewithin more difficult as compared to the conventional spike ports. For instance, the spike port resists the extraction of the spike from therewithin with a second minimal force which is greater than the first minimal force by at least three times. The second minimal force defines the minimum force required to extract the spike out of the spike port by overcoming the resistance, by virtue of friction and/or by locking as described according to a non-limiting example later herein below, offered by the spike port to the extraction when the medical spike is connected to the medical device.

In particular examples, the second minimal force can be at least four times, at least five times, or even at least six times greater than the first minimal force. In a particular example, the second minimal force can be as high as to resist the extraction so much as to effectively prevent the extraction of the spike from the spike port. The term prevent is intended to mean that the extraction is resisted up to an extent where the spike cannot be extracted from the spike port without most probably breaking, or damaging, at least one of the spike or the spike port. Although there can be a locking mechanism that locks the spike and resists the extraction thereof as effectively as the one described herein but without damaging the spike or the port upon extraction, and all such locking mechanisms be considered within the scope of the present application.

According to some examples, the first minimal force can be at most 40N at an insertion rate of 500 mm·min$^{-1}$, when tested with a test spike in accordance with ISO 8536-4, or can be at most 35N at an insertion rate of 500 mm·min$^{-1}$, when tested with a test spike in accordance with ISO 8536-4, or can be at most 30N at an insertion rate of 500 mm·min$^{-1}$, when tested with a test spike in accordance with ISO 8536-4, or can be at most 25N at an insertion rate of 500 mm·min$^{-1}$, when tested with a test spike in accordance with ISO 8536-4.

In accordance with the above-mentioned examples of the first minimal force, the second minimal force can be at least 120N (when the first minimal force is 40N) when measured with the same test spike as used for measurement of the first minimal force and at a removal speed of 100 mm·min$^{-1}$, or can be at least 105N (when the first minimal force is 35N) when measured with the same test spike as used for measurement of the first minimal force and at a removal speed of 100 mm·min$^{-1}$, or can be at least 90N (when the first minimal force is 30N) when measured with the same test spike as used for measurement of the first minimal force and at a removal speed of 100 mm·min$^{-1}$, or can be at least 75N (when the first minimal force is 25N) when measured with the same test spike as used for measurement of the first minimal force and at a removal speed of 100 mm·min$^{-1}$, or can be at least 140N, 150N, or 175N (when the first minimal force is at most 40N) when measured with the same test spike as used for measurement of the first minimal force and at a removal speed of 100 mm·min$^{-1}$.

Accordingly, the spike port is configured for offering a very low resistance to insertion of the spike into the spike port and simultaneously offer a very high resistance to the extraction thereof. In fact, the spike port according to the presently disclosed subject matter eliminates the need for friction between the inner surface of the spike port and the spike for resisting the extraction of the spike. The friction can be reduced inasmuch as that lubricants such as silicone oil and/or low resistance materials like Teflon can be used at the inner portions of the spike port that comes in contact with the spike to reduce the resistance offered by the spike port to the spike during insertion thereof. Accordingly, the resistance to extraction is achieved by a locking mechanism (described in detail later herein below) instead of the friction as in conventional spike ports. Such locking provides an improved resistance to extraction of the spike which is much desired and necessary in the drug transfer systems especially the ones dealing with hazardous drugs.

It is to be understood herein that resistance to insertion is intended to mean the resistance offered by the spike port to insertion of the spike therewithin when the spike is almost fully inserted into the spike port, and that resistance to extraction is intended to mean the resistance offered by the port to extraction of the spike from the port at the beginning of extraction, i.e., as soon as the extraction force (manual or natural, axial and/or rotational) is applied. In other words, the resistance to insertion even when the spike is almost fully inserted into the port is significantly lesser than the resistance to extraction even at the beginning (initiation) of the extraction.

Also, the term 'at least resist' is intended to include within the scope thereof the above-mentioned meaning of term prevent.

It is to be understood herein that the extraction force/action of the spike from the spike port 102 includes intentional (e.g. by pulling), unintentional extraction force/action such as jerk etc., and natural forces such as gravitation, and the force includes axial as well as rotational forces, in alternative or in addition to the axial forces. Reference is now made to FIGS. 2A to 4D to explain in detail the above-mentioned operation of the spike port 102. In order to resist the extraction of the spike from the spike port 102, according to the illustrated example, the spike port 102 includes the locking mechanism 110. The spike-locking mechanism 110 is configured to resist extraction of the spike from the spike port 102 when the spike is at least partially received within the spike port 102, at least to an extent at which an outer surface of the spike contacts the spike-locking mechanism 110.

The spike-locking mechanism 110 is configured to be activated, to thereby lock the spike inside the spike port 102, in response to initiation of extraction of the medical spike out of the spike port 102. It is to be understood herein that for the purposes of this description, the term activated with respect to the locking mechanism is intended to mean a state at which the locking mechanism grabs the spike tight enough to at least resist the extraction thereof from the port, and the term locking is intended to mean grabbing the spike tight enough to at least resist the extraction thereof from the port. Although the locking mechanism is in contact with the spike even before the activation thereof, yet the locking mechanism grabs the spike tight enough to resist its extraction only upon activation and that is when the locking mechanism locks the spike. The spike-locking mechanism 110 is configured to be activated automatically upon application of the extraction force, or in other words in response to the application of extraction force. The only action required for the activation of the spike-locking mechanism is a first application of the extraction force.

The spike-locking mechanism 110 is almost transparent with regard to insertion of the spike and minimally interact with, i.e., just contact, the spike when the latter is being inserted into the spike port 102, in such a way to not harden the insertion of the spike into the spike port, or while being located thereinside, and it only comes into action, i.e., activated when an extraction action is involved, as will be further exemplified herein below. Accordingly, the spike-locking mechanism 110 is configured as having two states, namely an unlocking state in which insertion of the medical spike into the spike port 102 is allowed and a locking state in which extraction of the medical spike from the spike port 102 is at least resisted. Therefore, the spike-locking mechanism 110 may switch from the unlocking state to the locking state once an extraction force is initiated. It is to be understood herein that activation of the spike-locking mechanism is intended to have same meaning as the spike-locking mechanism switching to its locking state.

As shown in FIGS. 2A and 2B, the medical device includes a port cover member 130 that selectively covers the port inlet 104 when no spike is inserted into the spike port 102 and uncovers the port inlet 104 to enable insertion of the spike thereto. It is appreciated that the port inlet 104 can be attached to the body portion 100 in a variety of ways. For example, it can form an integral part of the body portion 100. In another example, it can be detachably attachable to the body portion 100. In the described example, the port inlet 104 includes a plurality of pockets 132 (generally at least two) that form part of a snap-fit connection and are connected to matching arms 134 extending proximally from the body portion 100.

In some embodiments, the spike-locking mechanism 110 includes at least one spike-locking element positioned between the port inlet 104 and a distal end 1021 of the spike port 102. In the described example, the spike-locking mechanism 110 includes a spike-locking element 1101. Generally, the spike-locking element(s) can be positioned at any point along the port longitudinal axis between the port inlet and the distal port end. In the described non-limiting example, the spike-locking element 1101 is positioned closer to the port inlet 104 than to the distal port end 1021. This configuration can be advantageous for integrating the spike-locking mechanism 110, specifically the spike locking element 1101, into any spike port in general. Further, this positioning provides an aid in preventing debris, potentially resulting from the spike locking action when the spike-locking element 1101, as will be further described below, locks on the outer surface of the spike, to be released into the drug and to be transferred through the spike to the patient.

In some embodiments, as will be further described below, the spike port includes a seating portion that is configured to accommodate the spike-locking element within the spike port and allow free rotation of the spike-locking element therein. Allowing free rotation of the spike-locking element enhances the locking of the spike and resists its extraction, because it cancels the option of extracting the spike by rotating the spike in the spike port.

Figure 2C:
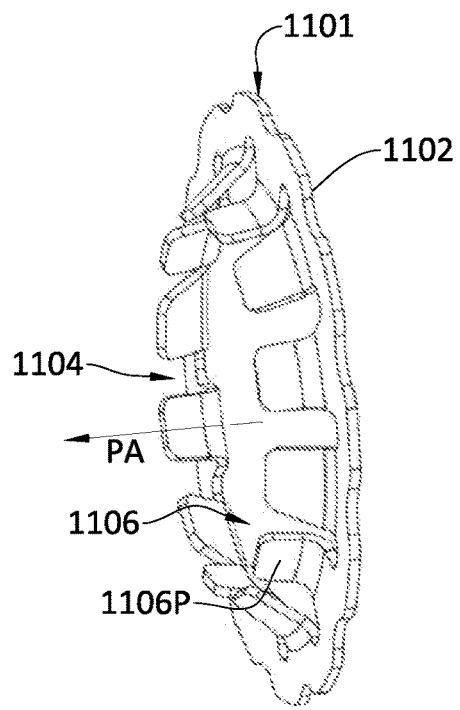
FIGS. 2C to 2F are different enlarged views of the spike-locking element.
Figure 2D:
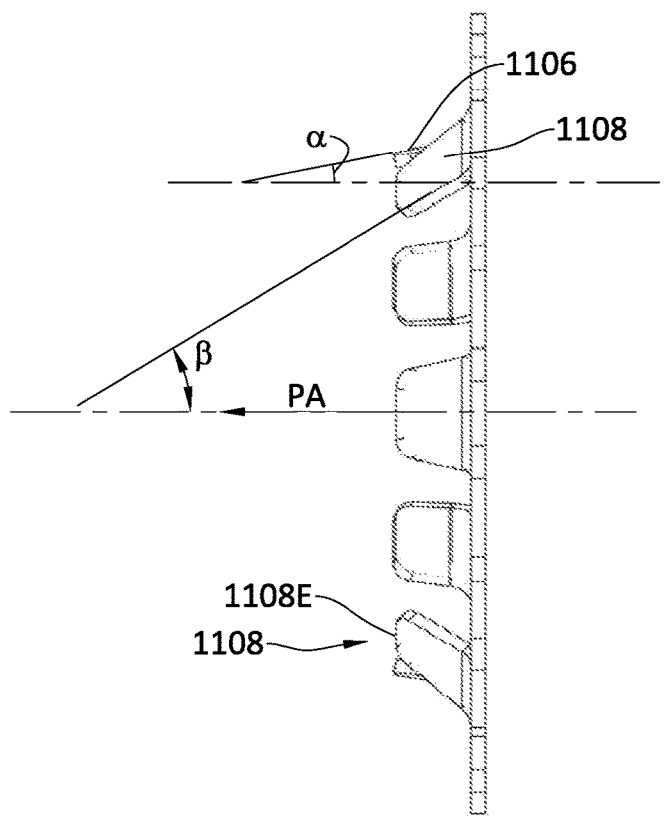
Figure 2E:
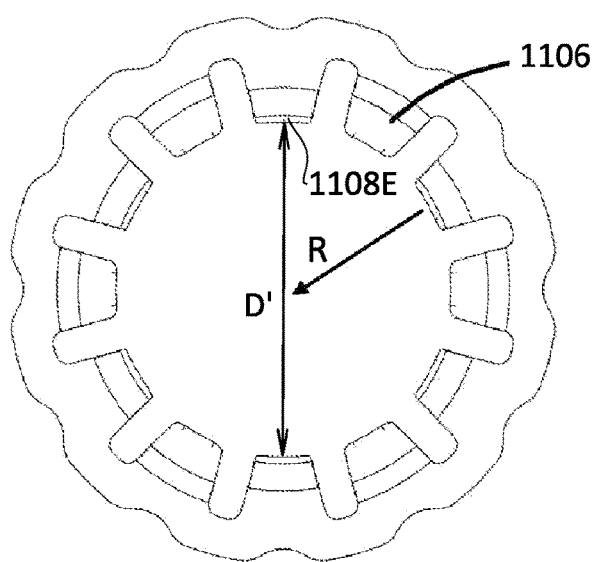
Figure 2F:
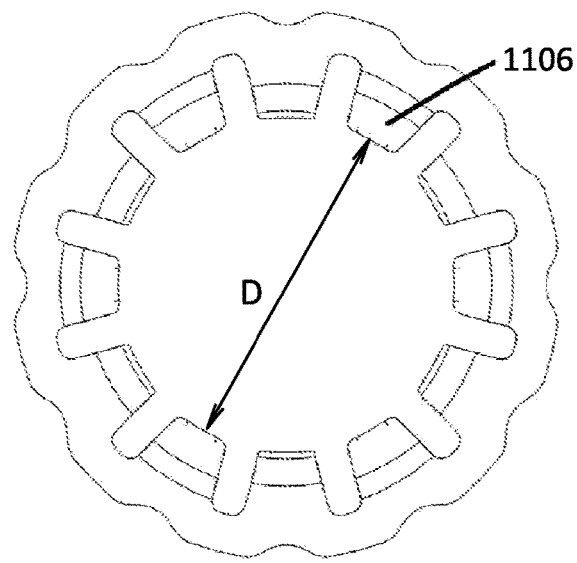

Reference is made to FIGS. 2C-2F showing different views of the spike-locking element 1101. FIG. 2C is a perspective view, FIG. 2D is a side view, FIG. 2E is a front view as seen from the distal side of the spike port), and FIG. 2F is a back view (as seen from the proximal side of the spike port). The spike-locking element 1101 includes an outer rigid portion 1102 that allows the element's positioning in the spike port 102, typically contacting the inner surface of the spike port 102, and a movable portion 1104 that extends radially inwardly, i.e., towards the longitudinal axis PA as well as towards the distal side of the port, from the rigid portion 1102, and is configured to move further towards the longitudinal axis PA and away from the distal side of the port (i.e., towards the port inlet 104) upon initiation of extraction of the medical spike out of the spike port 102. The rigid portion has an outer shape that enables the spike-locking element to rotate inside the spike port. In some non-limiting examples, the rigid portion has an annular shape tracing the circular cross-section of the spike port's lumen. In this example, the rigid portion 1102 has a semicircular symmetrical outer shape to reduce contact with the surroundings, and consequently allow smoother rotation with the locked spike, when located inside the spike port. The movable portion 1104 moves along at least a radial direction R of the spike port 102 towards the port longitudinal axis PA of the spike port 102. In some embodiments, the movable portion of the spike-locking element includes at least one first inwardly projecting element inclined respectively with at least one first element angle defined with respect to a proximal portion of the port longitudinal axis and having respectively at least one first element distal portion that contacts the outer surface of the spike when received inside the spike port 102. In the described example, the spike-locking element 1101 includes a plurality of first inwardly projecting elements 1106, namely six first projecting elements, inclined respectively with at least one first element angle α defined with respect to a proximal portion of the port longitudinal axis PA and having respectively at least one first element distal portion 1106P. The at least one first projecting element 1106 is configured to be activated by increasing the at least one first element angle α upon application of an extraction force causing initiation of extraction of the medical spike out of the spike port such that the first element distal portion tightens its contact with the outer surface of the medical spike and resists the extraction of the medical spike from the spike port. For instance, when the spike is inserted into the spike port 102, the outer surface of the spike contacts the first element distal portions 1106P. Upon initiation of extraction of the spike, the spike tends to move (or slightly moves) out of the spike port 102 thereby causing the first element distal portions 1006P to move, by virtue of pivoting of the first element distal portions 1106P at their respective connection points with the outer rigid portion to increase the first element angle α, in a direction towards the port longitudinal axis as well as away from the distal side of the spike port 102. Such movement causes the first element distal portions 1106P to tighten their contact with the outer surface of the spike thereby more tightly grabbing the spike to lock the spike inside the spike port. In some embodiments, the at least one first projecting element includes a plurality of first projecting teeth having a corresponding plurality of first tooth angles defining the at least one element angle and a corresponding plurality of first tooth distal portions defining the at least one first element distal portion.

In some embodiments, the movable portion of the spike-locking element includes at least one second projecting element having respectively at least one second element angle, defined with respect to the proximal portion of the port longitudinal axis, being greater than the at least one first element angle of the at least one first projecting element, and having respectively at least one second element distal edge. In the described example, the movable portion 1104 of the spike-locking element 1101 includes six second projecting elements 1108, each having respectively at least one second element angle (3, defined with respect to the proximal portion of the port longitudinal axis PA, it is greater than a and has at least one second element distal edge 1108E that contacts the outer surface of the medical spike when activated. The second projecting elements 1108 are operatively connected to the first projecting elements 1106 in a way such that in response to initiation of the extraction of the medical spike out of the spike port, the at least one first element 1106 moves as described above causing the at least one second projecting element 1108 to move at least towards the port longitudinal axis and the at least one second element angle to increase, thereby causing the at least one second element distal edge to contact the outer surface of the medical spike, thereby further resisting the extraction of the spike from the spike port. For instance, the second projecting elements 1108 are operative connected to the first projecting elements 1106 via the outer rigid portion. Therefore, the above-mentioned movement of the first projecting elements in response to initiation of extraction, the second projecting elements 1108 also move at least in the direction towards the longitudinal axis PA causing the second element angle θ to increase thereby causing the second element distal edges 1108E to contact the outer surface of the spike and further restricting the extraction of the spike. Further application of the extraction force causes the second elements 1108 to move further and the second element angle (3 to increase further, thereby causing the second element distal edges 1108E to incise into the outer surface of the spike, thereby further tightly resisting the extraction of the spike from the spike port. In some embodiments, the at least one second projecting element comprises a plurality of projecting legs having a corresponding plurality of leg angles defining said at least one second element angle and a corresponding plurality of leg distal edges defining said at least one second element distal edge. Further, in the described example, each of the second projecting elements 1108 is surrounded by two adjacent projecting elements 1106 (one of either side). In some examples, the number of the projecting elements 1106 can be different from the number of the second projecting elements 1108. The first projecting elements act as the main locking points and the second projecting elements acts as the auxiliary locking points, and are more aggressive lockers than the first projecting elements. In some examples, the locking element, or at least the second projecting elements are made of material hard/rigid enough to incise into the surface of the spike, for example metal.

Typically, the spike-locking mechanism contacts the spike during the insertion phase and locks the spike inside the spike port in response to initiation of extraction. Specifically, the spike-locking mechanism may apply first and second resistance forces on the medical spike during respectively the insertion and extraction of the medical spike into and out of the spike port, where the first resistance force is negligible (or at least three times lesser) with respect to the second resistance force as described above. In the described example, a diameter D defined by a virtual circle inscribed by the first projecting elements is smaller than a diameter D' of a similar virtual circle inscribed by the second projecting elements, thereby causing the first projecting elements to engage the spike first and the second projecting elements engage the spike only upon activation of the locking mechanism. In other examples, both these diameters can be equal. This contact between the first projecting elements during insertion of the spike also stabilizes the spike inside the spike port, and in this case the spike-locking elements takes part as a spike stabilizer.

As described above with reference to FIG. 2A, the spike port 102 includes a seating portion 106 that accommodates the spike-locking element 1101, specifically the rigid portion 1102. Specifically, the seating portion 106 is formed as a groove in the inner surface of the spike port that accommodates the rigid portion of the spike-locking element while keeping it able to rotate inside the port, and by this enhances the locking of the spike when it rotates together with the spike when the spike is subjected to rotational extraction force, therefore resisting the spike from being extracted from the spike port by rotating the spike. In the illustrated example, one wall of the groove 106 is formed by the port inlet 104, however in some examples, where the port inlet may not be structured in the manner described here, and the most proximal opening of the spike port acts as port inlet without the reduced diameter as depicted here, the groove can still be formed in the inner surface of the spike port.

Although the locking mechanism, and more particularly the locking element, has been illustrated herein as a continuous annular structure, it is to be understood herein that in some examples, the locking mechanism can have discrete projecting elements distributed about the longitudinal axis in the seating portion and configured to operate in the same manner as the locking element described above. In other examples, the locking mechanism can have a structure different from the structure as described above while being configured to serve the above-described purpose.

Reference is now made to FIGS. 3A-3D to explain in detail the above-mentioned features about easy insertion of the spike into the spike port 102. As mentioned above, the medical device 10 includes a spike port configured to receive therein a medical spike and establish therewith a fluid communication. It is noted that while the medical device 10 can incorporate both of the above-described aspect concerning the spike-locking mechanism as well as the aspects described herein below concerning easy insertion, stabilizing and sealing of the spike within the spike port, it can incorporate either independently. The described example herein should not be construed as limiting the different and distinct, yet combinable, aspects of the disclosed subject matter.

Figure 3A:
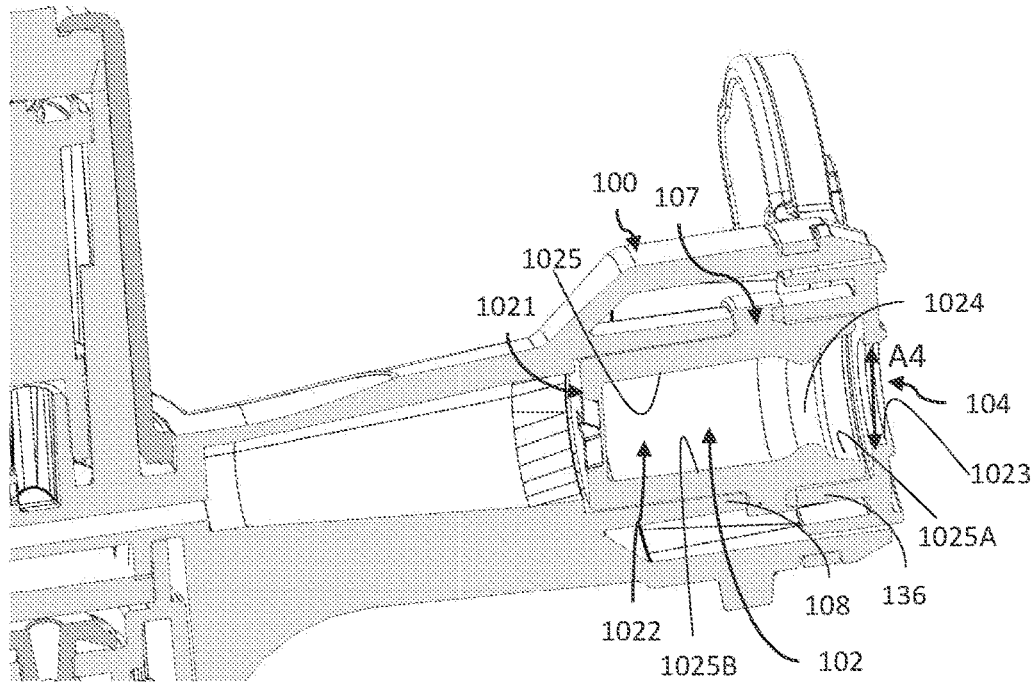
FIG. 3A is an enlarged view of the cross-sectional view of FIG. 1B, illustrating a non-limiting example of a spike port including port sealing and spike stabilizing elements according to a second aspect of the presently disclosed subject matter.

According to the below description, a solution to the required large and challenging spike insertion forces and spike safe holding requirements mentioned above is provided. As shown in FIG. 3A, illustrating an enlarged view of a perspective cross-section along line A-A of FIG. 1A, the medical device 10 includes the spike port 102 that includes a port distal portion 1022 provided in a closed state at the closed region constituted by a port distal end 1021 and which is configured to be opened by the spike's distal end during insertion of the medical spike into the spike port 102. The closed region can, in other examples, be at other regions of the spike port. The spike port 102 also includes a port proximal portion 1023 including the port inlet 104 and which is configured to stabilize the medical spike when received inside the spike port 102, and at least one sealing element 1024 located between from the port distal portion 1022 and the port proximal portion 1023. In some examples, the spike port may not include a port inlet as the one described herein (i.e., with a reduced diameter as compared to its adjacent portion), and an open proximal end (without the reduced diameter) can act as the port inlet. In such examples, the stabilizing can be achieved by the locking mechanism positioned in a seating portion formed in the form of a groove in the proximal portion of the spike port.

The sealing element 1024 is configured to seal the spike port 102 and prevent leakage therefrom through the port inlet 104. It is to be understood herein that the sealing element 1024 functions only as a sealing element without substantially contributing to the stabilizing, which is provided either by the port inlet and/or by the locking mechanism. The sealing element 1024 is configured to seal the interior of the spike port from the exterior of the spike port in such a manner that when a test spike, in accordance with ISO 8536-4, remain inserted in the spike port for 5 hours, and then an interior of the spike port distal to the sealing element is subjected to gauge pressure of 20 kPa for 15 seconds, no leakage occurs. As mentioned above, separating between the stabilizing and sealing functions, that are generally assigned to the port inlet in the common practice, enables reducing the insertion force that is required to overcome large friction forces all the way into the spike port, by reducing the contact surface between the spike port and the spike at one side, and by enabling using different materials having different stiffness and flexibility properties at the other side. Accordingly, the friction can even further be reduced by using a low friction material like Teflon and/or using lubricants like silicone oil at the sealing element, thereby eliminating to a large extent friction between the spike port and the spike, while achieving the resistance to extraction by the locking mechanism as described above.

As shown, the spike port 102 has a port inner surface/lumen 1025 that includes a proximal port inner surface 1025A corresponding said port proximal portion 1023 and extending between the port inlet and the at least one sealing element 1024 and a distal port inner surface 1025B corresponding said port distal portion 1022 and extending between the at least one sealing element 1024 and the port distal end. The port inner lumen is basically circular and symmetrical. In this case, each one of the port inlet 104 and the at least one sealing element 1024 defines respectively an inlet minimal diameter A4 at a cross-section taken at the proximal port inlet perpendicular to the longitudinal axis and a sealing minimal diameter A2 at a cross-section taken at the sealing element 1024 perpendicular to the longitudinal axis. The sealing minimal diameter A2 is smaller than the inlet minimal diameter A4. Each one of the proximal port inner surface portion 1025A and the distal port inner surface portion 1025B defines respectively a proximal maximal diameter A1 at a cross-section taken at the proximal portion (specifically at the seating portion) perpendicular to the longitudinal axis and a distal maximal diameter A3 at a cross-section taken at the distal portion (specifically adjacent said sealing element) perpendicular to the longitudinal axis. The proximal maximal diameter A1 being greater than the distal maximal diameter A3. Also, the proximal maximal diameter A1 is greater than both the inlet minimal diameter A4 and the sealing minimal diameter A2. The sealing minimal diameter A2 is smaller than the distal maximal diameter A3. This way, the contact surface between the spike and the spike port's inner lumen 1025 is either non-existing or at least reduced resulting in reduced friction forces and consequently reduced spike insertion force.

When the spike is fully received in the spike port, the spike sealing element fully surrounds the medical spike, thereby sealing the spike port and preventing fluid leakage from the spike port via the port proximal portion to an exterior of the medical device. For example, the spike sealing element is a ring having an annular shape, such as in the described example, that contacts the whole circumference of a ring section of the outer surface of the spike. In other words, the spike sealing element circumferentially envelopes a portion of the medical spike, i.e. fully covers, and tightly engages, a circular section of the outer surface of the spike when received inside the spike port.

In the described example, the at least one spike sealing element 1024 is formed as a protrusion extending radially inwardly from the port inner surface 1025 towards the port longitudinal axis PA.

In some embodiments, the at least one spike sealing element forms an integral part of the port inner surface, such as in the described example. In some embodiments, the at least one spike sealing element is a separate element, such as a ring, that is inserted and attached to the port's inner surface in a transverse direction to the port longitudinal axis.

In some embodiments, the at least one sealing element is made from a resilient material, thereby reducing the friction forces further. On the other side, the stabilizing element that forms at least a part of the port proximal portion is made from harder, stiffer, material to hold the spike securely in place. In the described example, the stabilizing element is basically the spike-locking mechanism 110.

Figure 3B:
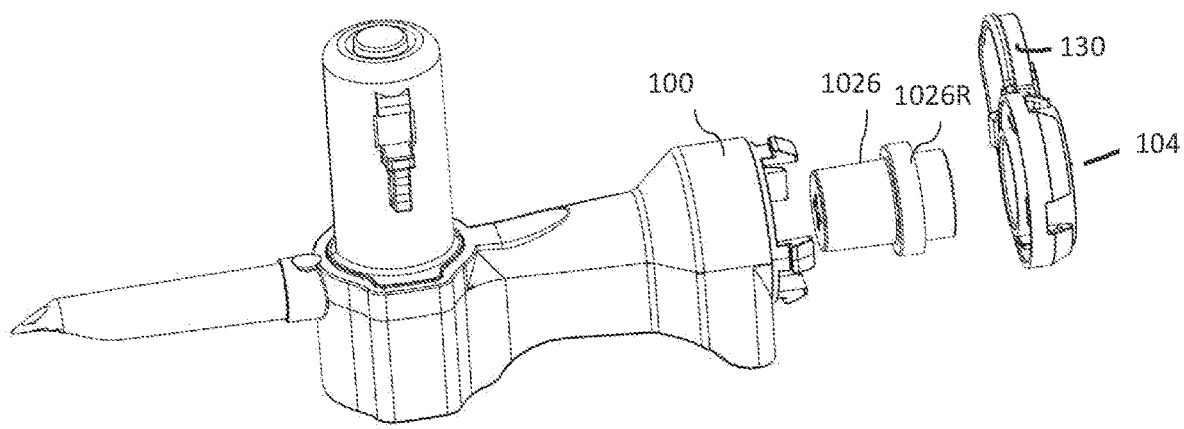
FIG. 3B is an exploded perspective view of the medical device of FIG. 1A, illustrating a non-limiting example of the spike port in accordance with the presently disclosed subject matter.
Figure 3C:
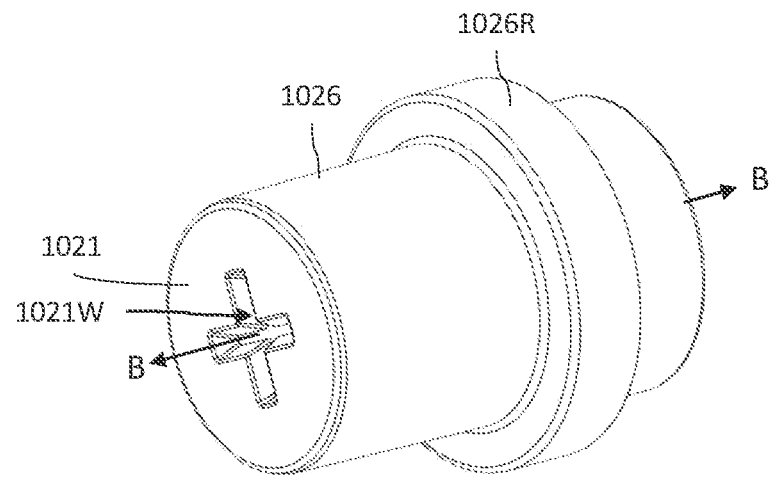
FIG. 3C is an enlarged view of the spike port.
Figure 3D:
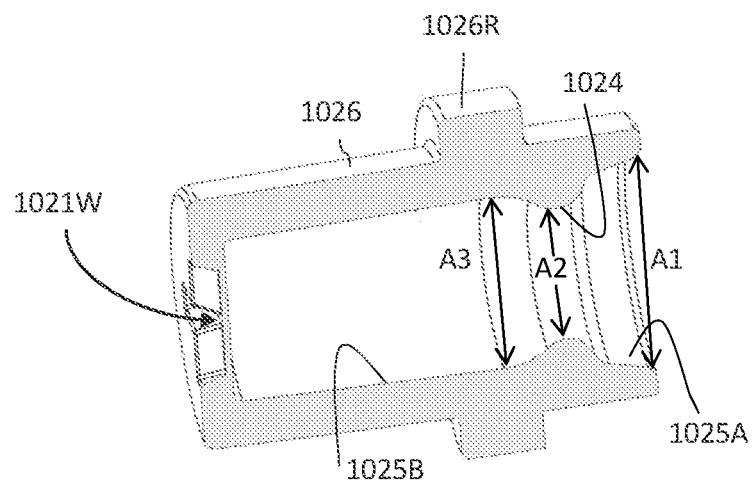
FIG. 3D is a cross-sectional view of the spike port, along line B-B in FIG. 3C.

In some embodiments, the port distal portion, the at least one sealing element and the port inner surface are formed as a unitary body/unibody member. This can be advantageous in the manufacturing process using, for example, molding techniques. In one example, the unibody member is made from a resilient material. In some embodiments, the resilient material is a thermoset. In the described example, as shown in FIGS. 3B-3D, where FIG. 3B illustrates a partial exploded perspective view of the body portion 100, FIG. 3C illustrates one form of the spike port and FIG. 3D is a cross-sectional view of FIG. 3C along the line B-B, the spike port, apart from the port proximal portion that is constituted at least partially by the port cover member 130, has a unibody shape 1026, the port distal portion 1022 (including the port distal end 1021), the sealing element 1024 and the port inner surface 1025. The unibody 1026 is securely received inside the body portion 100 (the spike receiving portion). In the described example, the unibody 1026 includes an integral ridge portion 1026R in a ring form that is received in a matching recess 107 in the body portion 100. This securely fixes the port unibody 1026 in place without any need for glue materials and enables manufacturing the port unibody from drug-compatible, soft, resilient materials, such as a thermoset material, specifically silicon. As can be seen in the figures, the port unibody 1026 is held securely in place by the attachment of the port inlet 104 to the body portion 100 (using a snap-fit connection) from the proximal side (the right side in the illustrated figures). Accordingly, the port inlet 104 includes a circular rim 136 that is pushed against the proximal side of the ridge 1026 and then the distal side of the ridge 1026R is pushed against a circular rim 108 formed in the body portion 100. This configuration enables attaching all the involved parts without using any glue material.

As mentioned above, the port distal portion/end is provided in a closed state to prevent leakage of drug from the medical device into the spike port before connecting the medical spike. Indeed, most of the times, connecting the medical spike is the last stage in order to establish the fluid connection through a fluid transfer system. In some embodiments, the port distal portion includes a plug configured to be pushed by the spike distal end during the insertion of the medical spike into the spike port, thereby opening the port distal portion. In some embodiments, the port distal portion includes a weakened region configured to be punctured by the spike distal end during the insertion of the medical spike into the spike port, thereby opening the port distal portion. In one example, the weakened region has a thickness being less than a nominal thickness of the port distal portion to facilitate its puncture by the spike distal end. In the described example, as shown in FIGS. 3C and 3D, the port distal end 1021 is provided in a closed state and includes a weakened region 1021W in the form of a depression having a cross shape, such that the wall is thinner than other regions of the port distal end, making it weaker and easier to tear out by the sharp distal end of the inserted spike.

Figure 4A:
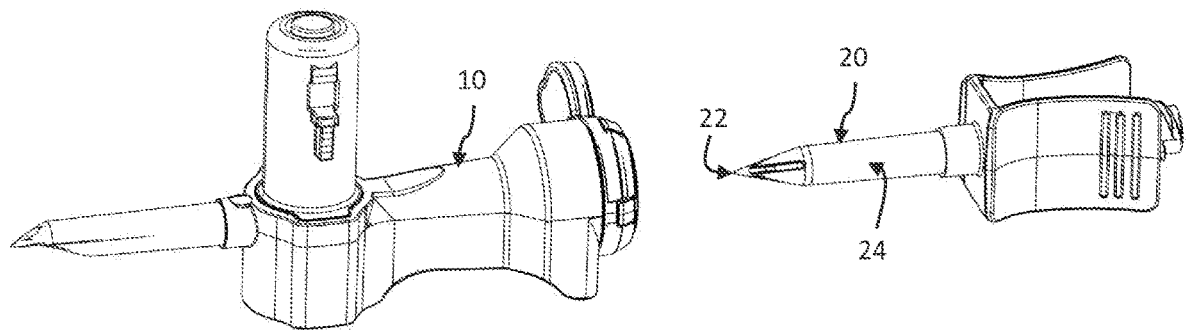
FIGS. 4A to 4D illustrate the insertion and locking of a spike inside the spike port configured in accordance with the presently disclosed subject matter.
Figure 4B:
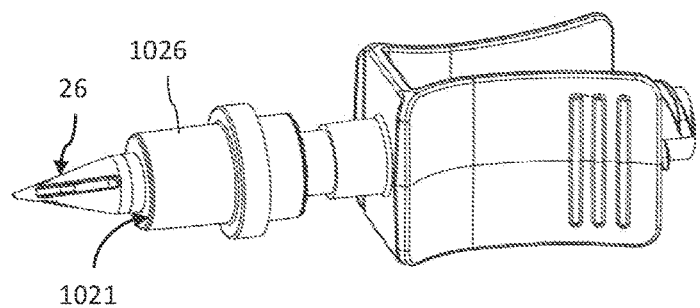
Figure 4C:
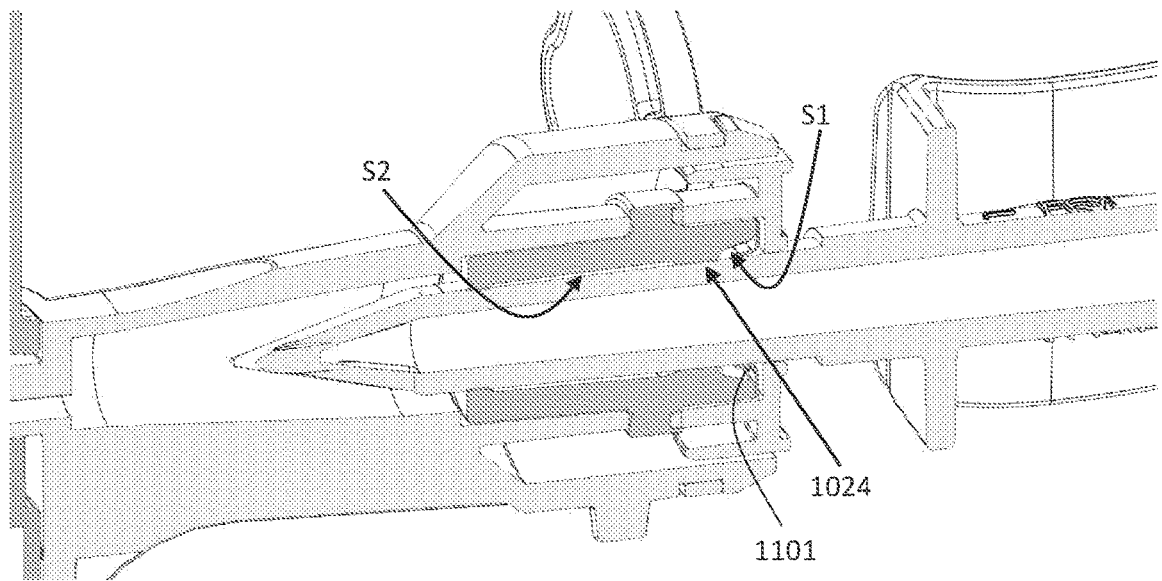

Reference is made to FIGS. 4A-4D illustrating the interaction between a spike 20 when inserted into the spike port 102 of the medical device 10. FIG. 4A shows the spike 20 approaching the medical device 10. The spike 20 has a spike distal end 22 configured to pierce or puncture the port distal end of the spike port, and an outer surface 24 through which the spike interacts with the sealing element and the spike locking element located in the spike port. FIG. 4B illustrates the situation when the spike 20 is fully inserted inside the unitary body 1026 of the spike port such that the distal portion of the spike 20 projects in the distal direction (towards the internal side of the device 10). FIG. 4C which is a cross-sectional enlarged view of the spike 20 located inside the spike port of device 10, illustrates how the resilient sealing element 1024 is pressed towards the circumference of the spike port by the outer surface 24 of the spike 20 such that a sealing of the port is achieved and no fluid is allowed to pass at least from the distal (internal) side of the spike port towards the proximal (outer) side of the spike port. Also illustrated in the figure are the spaces S1 and S2 between the outer surface 24 of the spike 20 and the inner surface (1025A and 1205B) before and after the sealing element 1024 respectively. The spaces S1 and S2 may not exist in every situation and their appearance or value depends, inter alia, on several factors such as the size of the spike, the value of the projection of the sealing element from the inner surface of the port.

Figure 4D:
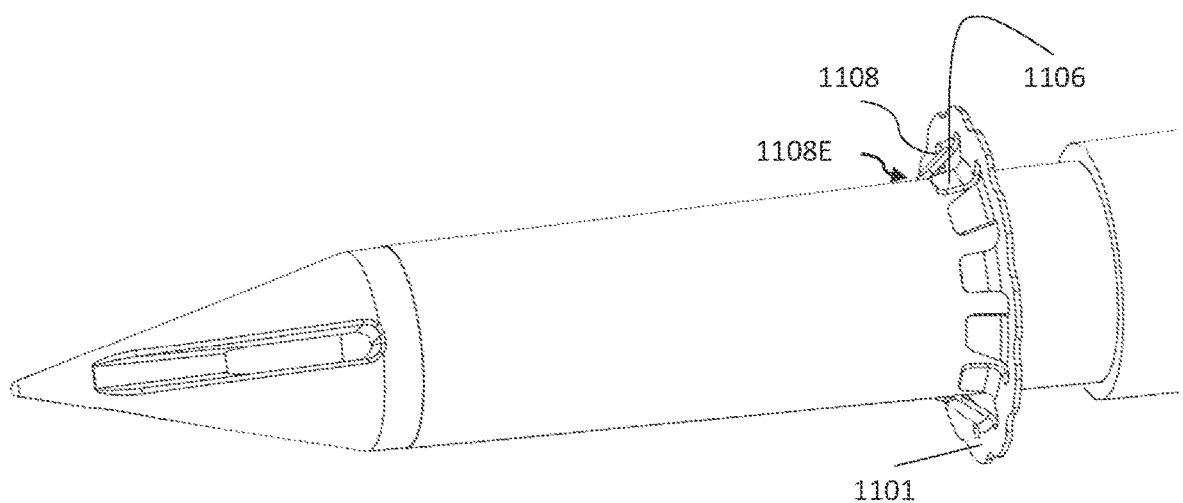

FIG. 4D illustrates the locking state of the spike-locking element 1101 that is activated when the spike 20 is received in the spike port and extraction of the spike is initiated.

Figure 5A:
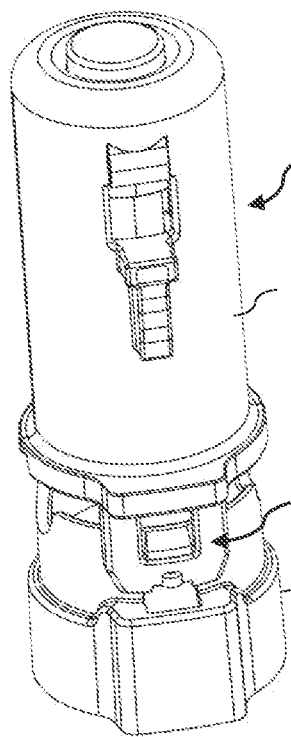
FIGS. 5A to 5C are enlarged views of a drug injection portion of the medical device of FIG. 1A, illustrating a third aspect of the presently disclosed subject matter.
Figure 5B:
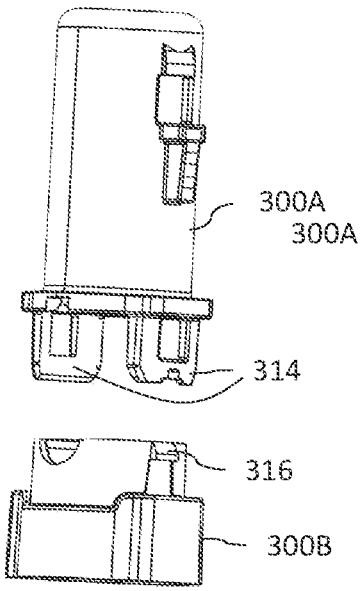
Figure 5C:
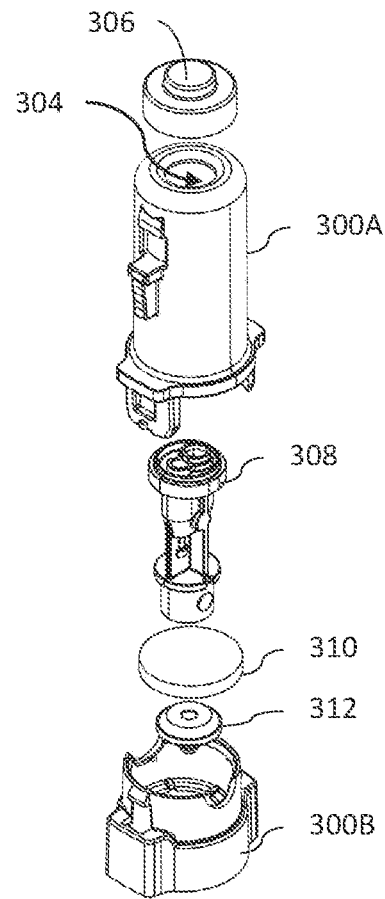

Reference is made to FIGS. 5A-5C Illustrating the medical device 10 with a third aspect of the presently disclosed subject matter. Again, it should be noted that while the third aspect is illustrated with reference to the medical device 10, this should not limit any of the described aspects of the presently disclosed subject matter to any specific configuration, any one of the aspects can be practiced independently or in combination with one or more of the described other aspects in the same medical device.

As described above, the medical device 10 includes a drug injection/transfer device 302 constituted by the body portion 300 and configured for transferring a drug therethrough in a contamination-free manner.

Drug transfer devices should be drug compatible, at least with regard to the device's parts that come in contact with the drug. Some of the prevalent drug compatible materials used in the production of drug transfer devices include thermoplastic materials such as polypropylene and PVC-free material. However, these drug compatible thermoplastic materials are relatively soft and have low stiffness, making building the whole body of the drug transfer device from the drug compatible thermoplastic materials challenging. Additionally, the drug transfer device frequently includes several functional elements that need to be combined together, preferably and sometimes inevitably without using glue material, and it is required that at least the housing of the device is rigid enough in order to hold the plurality of functional elements together. Yet additionally, some of the drug compatible materials are chemically inert, eliminating the possibility of being combined by being glued together. The presently disclosed subject matter provides an alternative approach for combining different elements into one device, e.g. utilizing a snap-fit connection.

As shown in the figures, the device 302 includes a housing 300 including at least two housing portions 300A and 300B connected to each other by a factory-set snap-fit connection 300C. At least one of the housing portions 300A and 300B is made from at least one first thermoplastic material that has high stiffness, such as Acetal. The first thermoplastic material forming the most outer housing portion need not be drug-compatible and can be drug-incompatible. The second housing portion can be made from the at least one first thermoplastic material or from at least one softer (having lower stiffness) second thermoplastic material. In some embodiments, the at least one second thermoplastic material has a lower magnitude of a physical property than that of the at least one first thermoplastic material, the physical property being at least one of the following: tensile strength, bending strength and hardness.

The device 302 also includes at least one element that is at least partially arranged inside the housing 300 and configured for passing the drug through the device. In the described example, there are a plurality of internal elements including at least one drug channel and at least one air channel (not specifically shown) housed in the element 308 which is received within the housing portion 300A, at least one air filter 310 and at least one one-way air valve 312 in communication with the at least one air channel in element 308. More details about such contamination-free drug transfer device can be found as mentioned above in WO08129550 assigned to the assignee of this application.

The elements that come in contact with the drug, such as the element 308, are made from a drug-compatible thermoplastic material which has at least one of the following properties: a relatively low stiffness, being chemically inert. In the described example, the element 308 is made from polypropylene. In some embodiments, the second thermoplastic material is a PVC-free material.

The snap-fit connection 300C holds the two housing portions 300 A and 300B.

The snap-fit connection can be a one fit connection that does not require taking the parts apart and does not require relative motion between the snap-fitted parts, neither before nor during or after use. the snap-fit connection can be formed by at least one snap connection element located on a first housing portion and at least one matching snap connection element located on a second housing portion. In some embodiments, the at least first housing portion includes protruding arms of the snap-fit connection, the protruding arms grasp corresponding snap-in portions formed in another housing portion of the at least two housing portions. In the described example, there are two similar protruding arms 314 on the first housing 300A and two respective matching snap-in portions 316 (one of them is not clearly shown) on the second housing 300B. The snap-fit connection 300C is meant for permanent, factory fitted, connection without a need for relative motion between the two housing portions.

The invention claimed is:

1. A medical device for fluidly connecting to a medical spike, the device comprising:
   a spike port having a proximal port inlet configured to receive therethrough the medical spike and establish fluid communication between the medical spike and the medical device, said spike port comprising a port longitudinal axis; and
   a spike-locking mechanism configured to resist extraction of the medical spike from the spike port, said spike-locking mechanism comprising a spike-locking element having an outer rigid portion and a movable portion extending inwardly from the outer rigid portion towards the port longitudinal axis and away from the proximal port inlet, said movable portion of the spike-locking element comprising:
      at least one first inwardly projecting element inclined with respective at least one first element angle defined with respect to a proximal portion of the port longitudinal axis and having respective at least one first element distal portion that contacts an outer surface of the medical spike when located in the spike port; and
      at least one second projecting element inclined with respective at least one second element angle defined with respect to the proximal portion of the port longitudinal axis, said at least one second element angle being greater than said at least one first element angle, said at least one second projecting element having respective at least one second element distal edge configured to contact the outer surface of the medical spike.

2. The medical device according to claim 1, wherein said spike-locking mechanism is configured to be activated, to thereby lock the medical spike inside the spike port for resisting the extraction thereof, in response to initiation of extraction of the medical spike out of the spike port, wherein said spike-locking mechanism is configured to be activated automatically in response to initiation of extraction of the medical spike out of the spike port.

3. The medical device according to claim 1, wherein said spike-locking mechanism is switchable from an unlocking state in which insertion of the medical spike into the spike port is allowed, and a locking state in which extraction of the medical spike from the spike port is resisted, wherein said spike-locking mechanism is switchable from said unlocking state to said locking state in response to initiation of the extraction of the medical spike out of the spike port.

4. The medical device according to claim 1, wherein the spike-locking mechanism is located inside the spike port, wherein said spike port comprises a distal port end and the port longitudinal axis extends between said proximal port inlet and distal port end, said spike-locking element being positioned between said proximal port inlet and said distal port end.

5. The medical device according to claim 1, wherein the movable portion is configured to contact the spike and move further towards the port longitudinal axis as well as the proximal port inlet upon initiation of extraction of the medical spike out of the spike port, thereby resisting the extraction of the spike from the spike port.

6. The medical device according to claim 1, wherein said movable portion moves along at least a radial direction towards said port longitudinal axis of the spike port.

7. The medical device according to claim 1, the at least one first inwardly projecting element being configured to be activated by increasing the at least one first element angle upon application of an extraction force causing initiation of extraction of the medical spike out of the spike port such that the first element distal portion tightens its contact with the outer surface of the medical spike and resists the extraction of the medical spike from the spike port.

8. The medical device according to claim 1, wherein said at least one first inwardly projecting element comprises a plurality of first projecting teeth having a corresponding plurality of first tooth angles defining said at least one first element angle and a corresponding plurality of first tooth distal portions defining said at least one first element distal portion.

9. The medical device according to claim 1, the at least one second projecting element being operatively connected to said at least one first inwardly projecting element in a way such that upon initiation of the extraction of the medical spike out of the spike port, the at least one first inwardly projecting element moves towards the port longitudinal axis as well as the proximal port inlet causing the at least one second projecting element to move at least towards the port longitudinal axis and the at least one second element angle to increase, thereby causing the at least one second element distal edge to contact the outer surface of the medical spike, thereby further resisting the extraction of the spike from the spike port.

10. The medical device according to claim 9, wherein upon further application of the extraction force, the at least second element distal edge is configured to incise into outer surface of the medical spike, thereby further tightly resisting the extraction of the spike from the spike port.

11. The medical device according to claim 1, wherein said at least one second projecting element comprises a plurality of projecting legs having a corresponding plurality of leg angles defining said at least one second element angle and a corresponding plurality of leg distal edges defining said at least one second element distal edge.

12. The medical device according to claim 1, wherein said spike port comprises a seating portion configured to accommodate said spike-locking element in the spike port and allow free rotation of the spike-locking element therein about the port longitudinal axis.

13. The medical device according to claim 1, wherein the spike port comprises a spike sealing element located between the proximal port inlet and a distal port end of the spike port.

14. The medical device according to claim 13, wherein said spike port has a port inner surface facing the port longitudinal axis, said port inner surface comprising a proximal inner surface portion extending between said proximal port inlet and said at least one spike sealing element, and a distal inner surface portion extending between said at least one spike sealing element and said distal port end, wherein at least one of at least a majority of the proximal inner surface portion and at least a majority of the distal inner surface portion being configured to be free of contact with the medical spike when received within the spike port.

15. The medical device according to claim 14, wherein said port inlet defines an inlet minimal diameter of a cross-section taken perpendicular to the port longitudinal axis, said spike sealing element defines a sealing minimal diameter of a cross-section taken perpendicular to the port longitudinal axis, and said proximal inner surface portion defines a proximal maximal diameter of a cross-section taken perpendicular to the port longitudinal axis, said proximal maximal diameter being greater than both the inlet and the sealing minimal diameters, wherein said distal inner surface portion defines a distal maximal diameter of a cross-section taken perpendicular to the port longitudinal axis, said distal maximal diameter being greater than the sealing minimal diameter.

16. The medical device according to claim 1, wherein said spike-locking element is more rigid than the proximal port inlet.

17. The medical device according to claim 1, wherein the spike-locking mechanism stabilizes the medical spike inside the spike port.

18. A spike-locking mechanism configured to be received within a spike port of a medical device and resist extraction of a medical spike when received within the spike port, the spike-locking mechanism being switchable from an unlocking state in which insertion of the medical spike into the spike port is allowed, and a locking state in which extraction of the medical spike from the spike port is resisted, the locking state is automatically activated upon initiating extraction of the medical spike out of the spike port, to thereby lock the medical spike inside the spike port, wherein said spike-locking mechanism comprises a spike-locking element having an outer rigid portion and a movable portion extending inwardly from the outer rigid portion towards a port longitudinal axis of the spike port and away from a proximal port inlet of the spike port, said movable portion of the spike-locking element comprising:
  at least one first inwardly projecting element inclined with respective at least one first element angle defined with respect to a proximal portion of the port longitudinal axis and having respective at least one first element distal portion that contacts an outer surface of the medical spike when located in the spike port; and
  at least one second projecting element inclined with respective at least one second element angle defined with respect to the proximal portion of the port longitudinal axis, said at least one second element angle being greater than said at least one first element angle, said at least one second projecting element having respective at least one second element distal edge configured to contact the outer surface of the medical spike.

19. The spike-locking mechanism according to claim 18, the at least one first inwardly projecting element being configured to be activated by increasing the at least one first element angle upon application of an extraction force causing initiation of extraction of the medical spike out of the spike port such that the first element distal portion tightens its contact with the outer surface of the medical spike and resists the extraction of the medical spike from the spike port.

20. The spike-locking mechanism according to claim 18, the at least one second projecting element being operatively connected to said at least one first inwardly projecting element in a way such that upon initiation of the extraction of the medical spike out of the spike port, the at least one first inwardly projecting element moves towards the port longitudinal axis as well as the proximal port inlet causing the at least one second projecting element to move at least towards the port longitudinal axis and the at least one second element angle to increase, thereby causing the at least one second element distal edge to contact the outer surface of the medical spike, thereby further resisting the extraction of the spike from the spike port, wherein upon further application of the extraction force, the at least second element distal edge is configured to incise into the outer surface of the medical spike, thereby further tightly resisting the extraction of the spike from the spike port.

* * * * *